US00PP24775P3

(12) United States Plant Patent
Zaiger et al.

(10) Patent No.: US PP24,775 P3
(45) Date of Patent: Aug. 19, 2014

(54) INTERSPECIFIC TREE NAMED 'LAGUNA'

(50) Latin Name: ***Interspecific Prunus* species**
Varietal Denomination: Laguna

(71) Applicants: Gary Neil Zaiger, Modesto, CA (US); Leith Marie Gardner, Modesto, CA (US); Grant Gene Zaiger, Modesto, CA (US)

(72) Inventors: Gary Neil Zaiger, Modesto, CA (US); Leith Marie Gardner, Modesto, CA (US); Grant Gene Zaiger, Modesto, CA (US)

( * ) Notice: Subject to any disclaimer, the term of this patent is extended or adjusted under 35 U.S.C. 154(b) by 80 days.

(21) Appl. No.: 13/694,603

(22) Filed: Dec. 17, 2012

(65) Prior Publication Data

US 2014/0173787 P1 Jun. 19, 2014

(51) Int. Cl.
*A01H 5/00* (2006.01)

(52) U.S. Cl.
USPC ..... Plt./180

(58) Field of Classification Search
USPC ..... Plt./180
See application file for complete search history.

*Primary Examiner* — Annette Para

(57) ABSTRACT

A new and distinct variety of interspecific tree. The following features of the tree and its fruit are characterized with the tree budded on 'Nemaguard' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1. Fruit with an attractive orange skin color.
2. Fruit with good flavor and eating quality.
3. Regular and productive bearer of medium to large size fruit.
4. Vigorous, upright tree growth.
5. Fruit with good handling and shipping quality.

1 Drawing Sheet

Botanical designation: Interspecific *Prunus* species.
Variety denomination: 'Laguna'.

BACKGROUND OF THE VARIETY

Field of the Invention

In the field of plant genetics, we conduct an extensive and continuing plant-breeding program including the organization and asexual reproduction of orchard trees, and of which plums, peaches, nectarines, apricots, cherries, almonds and interspecifics are exemplary. It was against this background of our activities that the present variety of interspecific tree was originated and asexually reproduced by us in our experimental orchard located near Modesto, Stanislaus County, Calif.

PRIOR VARIETIES

Among the existing varieties of apricot and interspecific trees, which are known to us, and mentioned herein, 'Flavor King' Interspecific (U.S. Plant Pat. No. 8,026), 'Autumn Glo' Apricot (U.S. Plant Pat. No. 9,864) and our proprietary non-patented apricot seedling selections '169LH391' and '35.5GH312'.

STATEMENT REGARDING FEDERALLY SPONSORED RESEARCH AND DEVELOPMENT

Not applicable.

ORIGIN OF THE VARIETY

The new variety of interspecific tree, a combination of crosses between (*Prunus armeniaca* and *Prunus salicina*)

was originated by us in our experimental orchard located near Modesto, Calif. from a cross between the proprietary non-patented apricot seedling selection with the field identification number '169LH391' and 'Flavor King' Interspecific (U.S. Plant Pat. No. 8,026). The seed parent '169LH391' apricot (non-patented) originated from an open pollinated seedling selection of '35.5GH312' apricot (non-patented) which is an open pollinated seedling selection from 'Autumn Glo' Apricot (U.S. Plant Pat. No. 9,864). A large number of these first generation seedlings were planted and maintained on their own root system. Under close and careful observation one such seedling, which is the present variety, exhibited desirable fruit and tree characteristics and was selected in 2003 for further asexual propagation and commercialization.

ASEXUAL REPRODUCTION OF THE VARIETY

Asexual reproduction of the new and distinct variety of interspecific tree was by budding to 'Nemaguard' Rootstock (non-patented), as performed by us in our experimental orchard located near Modesto, Calif., and shows reproductions run true to the original tree and all characteristics of the tree and its fruit are established and transmitted through succeeding asexual propagations.

SUMMARY OF THE NEW VARIETY

The present new and distinct variety of interspecific tree (*Prunus armeniaca*×*Prunus salicina*) is of large size, vigorous, upright growth and a regular and productive bearer of medium to large size, orange flesh, freestone fruit with good flavor and eating quality. The fruit is further characterized by having an attractive orange skin color, firm flesh with good handling and shipping quality. In comparison to its seed parent '169LH391' apricot (non-patented) the fruit of the new variety has orange flesh compared to yellow and is approximately 8 days later in maturity. In comparison to its pollen parent 'Flavor King' Interspecific (U.S. Plant Pat. No. 8,026) the fruit of the new variety is pubescent compared to glabrous, the flesh is orange compared to pale yellow-orange and freestone compared to semi-clingstone. In comparison to the commercial variety 'Late Brittney' (U.S. Plant Pat. No. 18,921) the fruit of the new variety is approximately 9 days later in maturity and has a darker orange skin color.

PHOTOGRAPH OF THE VARIETY

The accompanying color photographic illustration shows typical specimens of the foliage and fruit of the present new interspecific variety. The illustration shows the upper and lower surface of the leaves, an exterior and sectional view of a single fruit divided in its suture plane to show flesh color, pit cavity and the stone remaining in place. The photographic illustration was taken shortly after being picked (shipping ripe) from a 9 year old tree and the colors are as nearly true as is reasonably possible in a color representation of this type.

DESCRIPTION OF THE VARIETY

The following is a detailed botanical description of the new variety of interspecific tree, its flowers, foliage and fruit, as based on observations of 9 year old specimens grown near Modesto, Calif., with color in accordance with Munsell Book of Color published in 1958.

Tree:

*Size.*—Large, usually pruned to 3 to 3.5 meters in height and width for economical harvesting of fruit, varies with different cultural practices.

*Vigor.*—Vigorous, growth of approximately 1.5 to 2 meters the first growing season. Varies with type and fertility of soil, climatic conditions and cultural practices.

*Form.*—Upright, usually pruned to vase shape.

*Branching habit.*—Upright, crotch angle approximately 30°, increases with heavy crop load.

*Productivity.*—Productive, thinning and spacing of fruit necessary for desired marketable size. Fruit set varies with climatic conditions during blooming period.

*Bearer.*—Regular, has had adequate fruit set 7 consecutive years. No alternate bearing observed.

*Fertility.*—Self fertile, sets fruit under bag.

*Density.*—Medium dense, pruned to vase shape to allow sunlight to center of tree to enhance fruit color and health of fruit wood.

*Hardiness.*—Hardy in all stone fruit growing areas of California. Tree grown in USDA Hardiness Zone 9. Winter chilling requirement approximately 900 hours at or below 45° F.

Trunk:

*Size.*—Large. Average circumference 53.3 cm at 30.5 cm above ground on a 9 year old tree.

*Stocky.*—Medium stocky.

*Texture.*—Medium shaggy, roughness increases with age.

*Color.*—Varies from 2.5Y 5/2 to 5Y 5/2.

Branches:

*Size.*—Medium. Average circumference 21.1 cm at 1.2 meters above ground on a 9 year old tree. Crotch angle approximately 30°, increases with heavy crop load.

*Surface texture.*—New growth relatively smooth. Mature growth medium rough, roughness increases with age.

*Lenticels.*—Average number 26 in a 25.8 sq cm section. Average length 4.1 mm. Average width 2.1 mm. Color varies from 2.5Y 8/8 to 2.5Y 7/6.

*Color.*—New growth varies from 5GY 6/8 to 5GY 5/8. Old growth varies from 10YR 3/2 to 10YR 2/2, varies with age of growth.

Leaves:

*Size.*—Medium. Average length 74.5 mm. Average width 65.6 mm.

*Form.*—Ovate.

*Apex.*—Acuminate.

*Base.*—Obtuse.

*Margin.*—Serrulate.

*Thickness.*—Medium.

*Surface texture.*—Upper surface relatively smooth, very slightly indented over midrib and leaf veins. Lower surface relatively smooth, small ridges created by midrib and pinnate venation. Both upper and lower surfaces glabrous.

*Petiole.*—Average length 20.7 mm. Average width 1.2 mm. Longitudinally grooved. Surface glabrous. Color varies from 5GY 6/6 to 5GY 6/8, color varies with exposure to sunlight.

*Glands.*—Type — globose. Size — small. Number varies from 2 to 4, average number 3. Average length 0.5 mm. Average diameter 0.5 mm. Located primarily on upper portion of petiole and base of leaf blade. Color varies from 5GY 5/4 to 5GY 5/6.

*Stipules.*—Average length 5.1 mm. Average number 2. Edges — pectinate. Color varies from 5GY 7/4 to 5GY 6/4.

*Color.*—Upper surface varies from 7.5GY 4/4 to 7.5GY 3/4. Lower surface varies from 5GY 5/6 to 5GY 4/6. Midvein color varies from 5GY 8/6 to 5GY 7/6.

Flower buds:

*Size.*—Medium to large. Average length 12.8 mm. Average diameter 8.9 mm.

*Hardiness.*—Hardy with respect to California winters.

*Form.*—Conical, becoming elongated just before opening.

*Pedicel.*—Average length 2.6 mm. Average width 1.4 mm. Color varies from 2.5GY 7/8 to 10Y 7/10.

*Color.*—Varies from 5RP 9/2 to 10 RP 9/2.

*Number of buds per spur.*—Varies from 3 to 7, average number 5. Varies with age of spur.

Flowers:

*Blooming period.*—Date of First Bloom Feb. 24, 2012. Date of Petal Fall Mar. 6, 2012, varies slightly with climatic conditions.

*Size.*—Medium to large. Average height 17.1 mm. Average diameter 28.7 mm.

*Petals.*—Normally 5, alternately arranged to sepals. Size — medium to large. Average height 14.8 mm. Average width 14.8 mm. Form — orbicular. Margin — sinuate. Both upper and lower surfaces glabrous. Color N 9.5/ (white).

*Sepals.*—Normally 5, alternately arranged to petals. Size — large. Average length 6.4 mm. Average width 6.3 mm. Shape — ovate. Margin — entire. Surface — upper surface glabrous, lower surface pubescent. Color — upper surface varies from 5R 8/2 to 2.5R 3/10. Lower surface varies from 2.5R 3/10 to 5R 2/8.

*Stamens.*—Average number per flower 30. Average filament length 11.3 mm. Filament color N 9.5/ (white). Anther color varies from 5Y 8.5/10 to 5Y 8/10.

*Pollen.*—Self fertile, sets fruit under bag. Color varies from 5Y 7/12 to 5Y 8/14.

*Pistil.*—Normally 1. Surface — pubescent. Average length 17.5 mm. Position of stigma average of 2.0 mm above anthers. Color varies from 5Y 8/12 to 5Y 8.5/6.

*Fragrance.*—Slight.

*Color.*—Varies from N 9.5/ (white) to 5RP 9/2, depending on age of flower.

*Number flowers per flower bud.*—Average 1, varies from 1 to 2.

*Pedicel.*—Average length 3.4 mm. Average width 2.1 mm. Color varies from 10Y 7/8 to 7.5R 2/4.

Fruit:

*Maturity when described.*—Firm ripe.

*Date of first picking.*—Aug. 19, 2012.

*Date of last picking.*—Aug. 29, 2012, varies slightly with climatic conditions.

*Size.*—Medium to large. Average diameter axially 57.0 mm. Average transversely in suture plane 58.5 mm. Average across suture plane 52.6 mm. Average weight 93.7 grams, varies slightly with fertility of the soil, amount of thinning and climatic conditions.

*Form.*—Globose to slightly elongated.

*Suture.*—Lipped.

*Ventral surface.*—Lipped.

*Apex.*—Rounded to slightly retuse.

*Base.*—Retuse.

*Stem cavity.*—Rounded to slightly elongated in suture plane. Average depth 4.9 mm. Average diameter 5.6 mm.

Stem:

*Size.*—Small. Average length 7.6 mm. Average diameter 2.9 mm.

*Color.*—Varies from 10YR 3/6 to 7.5YR 3/6.

Flesh:

*Ripens.*—Evenly.

*Texture.*—Firm, meaty.

*Fibers.*—Few, small, tender.

*Firmness.*—Firm, comparable to commercial apricot varieties.

*Aroma.*—Moderate.

*Amydgalin.*—Undetected.

*Eating quality.*—Good.

*Flavor.*—Good.

*Juice.*—Slight amount, enhances flavor.

*Brix.*—Average Brix 12.5°, varies slightly with amount of fruit per tree and climatic conditions.

*Color.*—Varies from 5YR 6/8 to 5YR 6/10.

*Pit cavity.*—Average length 29.8 mm. Average width 24.0 mm. Average depth 7.5 mm. Color varies from 5YR 6/8 to 5YR 6/12.

Skin:

*Thickness.*—Medium.

*Surface.*—Smooth.

*Pubescence.*—Moderate pubescence, short in length.

*Tendency to crack.*—None.

*Color.*—Color varies from 5YR 5/10 to 5YR 5/12.

*Tenacity.*—Tenacious to flesh.

*Astringency.*—Slight to none.

Stone:

*Type.*—Freestone.

*Size.*—Large. Average length 28.2 mm. Average width 22.9 mm. Average thickness 15.1 mm.

*Form.*—Ovoid.

*Base.*—Flat.

*Apex.*—Round.

*Surface.*—Slightly pitted throughout, a shallow groove on each side of suture extending from base to apex.

*Sides.*—Unequal, one side extending further from suture plane.

*Ridges.*—Very narrow, a small ridge near groove on each side of suture.

*Tendency to split.*—None.

*Color.*—Varies from 2.5Y 4/4 to 10YR 4/4 when dry.

Kernel:

*Size.*—Large. Average length 21.0 mm. Average width 14.0 mm. Average depth 7.3 mm.

*Form.*—Ovoid.

*Viability.*—Viable, complete embryo development.

*Skin color.*—Varies from 7.5YR 4/8 to 7.5YR 4/6.

Use: Dessert.

*Market.*—Local and long distance.

Keeping quality: Good, held firm in cold storage at 38° to 42° F. for 3 weeks without internal breakdown of flesh or appreciable loss of flavor.

Shipping quality: Good, showed minimal skin scarring or bruising of flesh during picking, packing and shipping trials.

Plant/fruit disease resistance/susceptibility: No specific testing for relative plant/fruit disease resistance/susceptibility has been designed. Under close observation during planting, growing, and harvesting of fruit, under normal cultural and growing conditions near Modesto, Calif., no particular plant/fruit disease resistance or susceptibility has been observed. Any variety or selection observed during indexing of plant characteristics with abnormal fungus, bacterial, virus or insect susceptibility is destroyed and eliminated from our breeding program.

The present new variety of interspecific tree, its flowers, foliage and fruit herein described may vary in slight detail due to climate, soil conditions and cultural practices under which the variety may be grown. The present description is that of the variety grown under the ecological conditions prevailing near Modesto, Calif.

The invention claimed is:

1. A new and distinct variety of interspecific tree, substantially as illustrated and described.

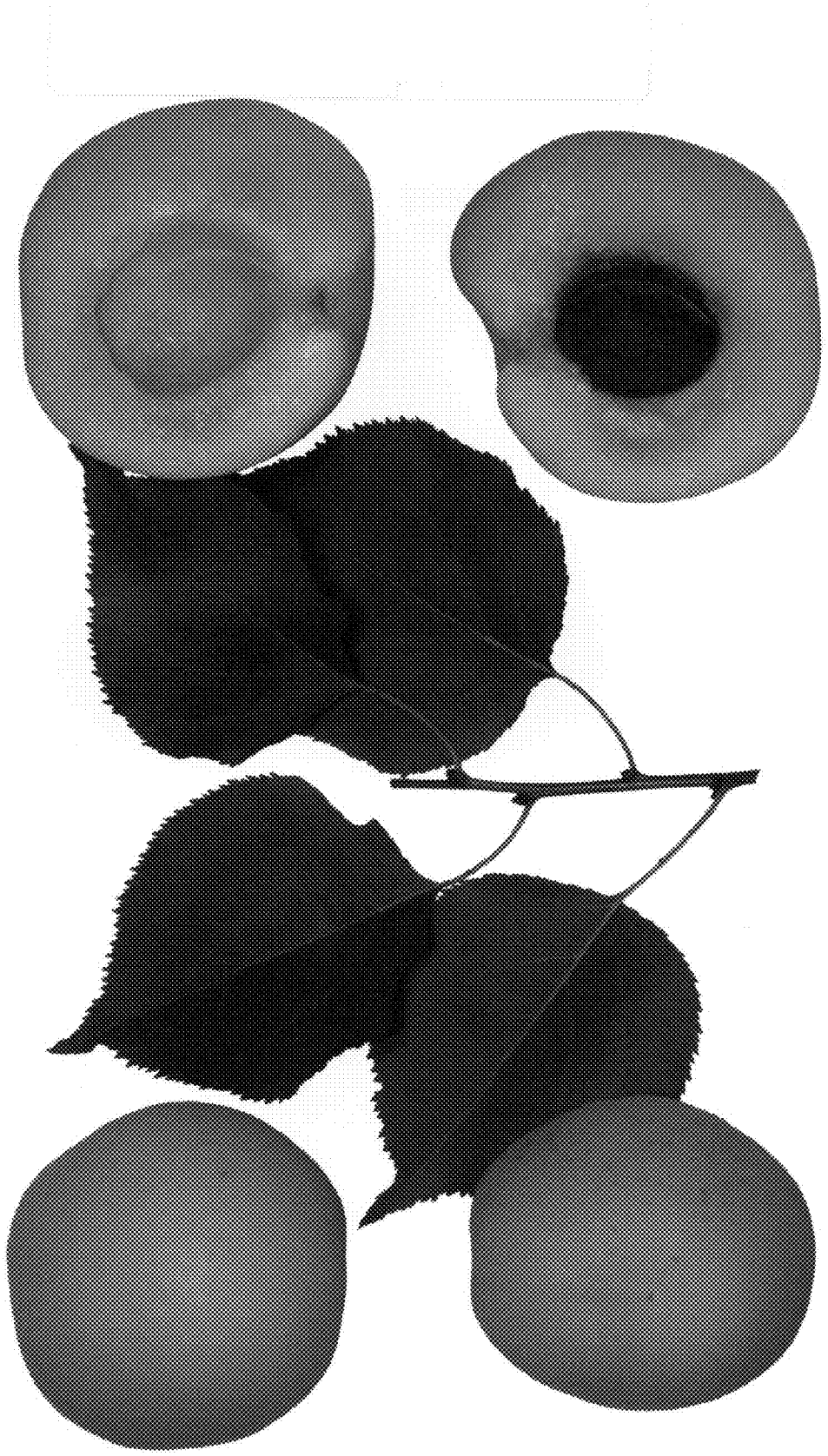

* * * * *